(12) United States Patent
Heath et al.

(10) Patent No.: US 9,005,377 B2
(45) Date of Patent: *Apr. 14, 2015

(54) METHOD OF MODIFYING A PHYSICAL PROPERTY OF AN ENDODONTIC INSTRUMENT

(71) Applicant: D & S Dental, LLC, Johnson City, TN (US)

(72) Inventors: Derek E. Heath, Vero Beach, FL (US); Steven J. A. Treadway, Jonesborough, TN (US)

(73) Assignee: D & S Dental, LLC, Johnson City, TN (US)

( * ) Notice: Subject to any disclaimer, the term of this patent is extended or adjusted under 35 U.S.C. 154(b) by 99 days.

This patent is subject to a terminal disclaimer.

(21) Appl. No.: 13/917,038

(22) Filed: Jun. 13, 2013

(65) Prior Publication Data

US 2013/0269841 A1 Oct. 17, 2013

Related U.S. Application Data

(63) Continuation-in-part of application No. 13/396,034, filed on Feb. 14, 2012, now Pat. No. 8,911,573, which is a continuation-in-part of application No. 12/950,536, filed on Nov. 19, 2010, now abandoned.

(60) Provisional application No. 61/658,959, filed on Jun. 13, 2012, provisional application No. 61/263,192, filed on Nov. 20, 2009.

(51) Int. Cl.
| | |
|---|---|
| C22F 1/10 | (2006.01) |
| C22F 1/00 | (2006.01) |
| A61C 5/02 | (2006.01) |
| C22F 1/18 | (2006.01) |
| C21D 1/26 | (2006.01) |

(52) U.S. Cl.
CPC ............... C22F 1/006 (2013.01); A61C 5/023 (2013.01); C21D 1/26 (2013.01); C22F 1/183 (2013.01); A61C 2201/00 (2013.01); A61C 2201/007 (2013.01); C21D 2201/01 (2013.01); C21D 2201/02 (2013.01); C22F 1/10 (2013.01)

(58) Field of Classification Search
None
See application file for complete search history.

(56) References Cited

U.S. PATENT DOCUMENTS

| | | |
|---|---|---|
| 4,889,487 A | 12/1989 | Lovaas |
| 5,464,362 A | 11/1995 | Heath et al. |
| 5,527,205 A | 6/1996 | Heath et al. |
| 5,628,674 A | 5/1997 | Heath et al. |
| 5,655,950 A | 8/1997 | Heath et al. |
| 5,762,541 A | 6/1998 | Heath et al. |
| 5,775,902 A | 7/1998 | Matsutani et al. |
| 5,820,375 A | 10/1998 | Chalifoux |
| 5,879,160 A | 3/1999 | Ruddle |
| 5,882,444 A | 3/1999 | Flomenblit et al. |
| 5,941,760 A | 8/1999 | Heath et al. |
| 6,042,376 A | 3/2000 | Cohen et al. |
| 6,149,501 A | 11/2000 | Farzin-Nia et al. |
| 6,315,558 B1 | 11/2001 | Farzin-Nia et al. |
| 6,579,092 B1 | 6/2003 | Senia et al. |
| 6,783,438 B2 | 8/2004 | Aloise et al. |
| 7,018,205 B2 | 3/2006 | Abel |
| 7,025,776 B1 | 4/2006 | Houser et al. |
| 7,137,815 B2 | 11/2006 | Matsutani et al. |
| 7,147,469 B2 | 12/2006 | Garman |
| 7,779,542 B2 | 8/2010 | Aloise et al. |
| 2002/0137008 A1 | 9/2002 | McSpadden et al. |
| 2004/0023186 A1 | 2/2004 | McSpadden |
| 2004/0117001 A1 | 6/2004 | Pelton et al. |
| 2006/0185169 A1 | 8/2006 | Lewis et al. |
| 2007/0054238 A1 | 3/2007 | Hof et al. |
| 2007/0137742 A1 | 6/2007 | Hao et al. |
| 2009/0130638 A1 | 5/2009 | Hof et al. |
| 2010/0233648 A1 | 9/2010 | McSpadden et al. |
| 2012/0208145 A1* | 8/2012 | Heath et al. .............. 433/102 |

FOREIGN PATENT DOCUMENTS

WO    2005070320 A1    8/2005

* cited by examiner

*Primary Examiner* — George Wyszomierski
(74) *Attorney, Agent, or Firm* — Luedeka Neely Group, P.C.

(57) ABSTRACT

Methods for modifying a physical characteristic of finished endodontic instruments made from one or more superelastic alloys is described which include heat treating one or more finished endodontic instruments in a salt bath for a specific time (e.g., from about four hours to about six hours), at a specified temperature (e.g., from about 475° C. to about 550° C.), and preferably at a specified pH range.

9 Claims, 4 Drawing Sheets

METHOD OF MODIFYING A PHYSICAL PROPERTY OF AN ENDODONTIC INSTRUMENT

CROSS-REFERENCE TO RELATED APPLICATIONS

This application claims priority to U.S. Provisional Application No. 61/658,959 filed on Jun. 13, 2012, U.S. Nonprovisional application Ser. No. 12/950,536 filed on Nov. 19, 2010 which claims priority to U.S. Provisional Application No. 61/263,192 filed on Nov. 20, 2009 and U.S. Continuation In Part application Ser. No. 13/396,034 filed on Feb. 14, 2012 which claims priority to U.S. Nonprovisional application Ser. No. 12/950,536 filed on Nov. 19, 2010 and U.S. Provisional Application No. 61/263,192 filed on Nov. 20, 2009 the entireties of which are incorporated herein by reference.

FIELD

This disclosure relates to the field of endodontic instruments. More particularly, this disclosure relates to endodontic instruments that have been treated in a salt bath to have limited memory physical characteristics, and methods for treating endodontic instruments in a salt bath.

BACKGROUND

Endodontic instruments made from alloys including Nickel Titanium are desirable because of various physical characteristics of such alloys. When heat treated, such alloys take on even more unique physical characteristics including, in some cases, limited memory wherein an instrument will partially rebound to its initial configuration after undergoing forced mechanical deformation.

Salt baths or salt solution technology at high temperatures (e.g., about 500° C.) have been used in stress-induced heating of endodontic blanks to bring such blanks to 100% austenite phase as discussed, for example, in U.S. Pat. No. 6,783,438 entitled "Method of Manufacturing an Endodontic Instrument" to Aloise et al. Such use of salt baths has been described as undesirable, however, in the U.S. Pat. No. 6,783,438 patent as well as, for example, U.S. Patent Publication Number 2010/0233648 entitled "Endodontic Instrument and Method of Manufacturing" to McSpadden et al. because of concerns of corrosion to the tooling or other materials involved in such treatments. For situations in which salt baths have been used to heat treat an endodontic blank, the exposure of the blank to the bath has been rapid, measured on scale of seconds as opposed to hours as taught, for example, in U.S. Pat. No. 6,149,501 entitled "Superelastic Endodontic Instrument, Method of Manufacture, and Apparatus Therefor" to Farzin-Nia et al.

In all of the examples given above, endodontic blanks (as opposed to finished endodontic instruments) were heat treated to acquire super elastic properties and then later cut to make finished endodontic instruments with cutting surfaces. Thus, the nature of the treatments in the prior examples included very limited treatment periods and specific timing regarding the phase of the overall manufacturing process in which heat treatment occurred.

SUMMARY

Despite the various teachings against using salt baths in general, Applicants have discovered a method to heat treat finished endodontic instruments using salt baths for an extended period of time in order to invoke limited or "controlled" memory properties in such endodontic instruments when the instruments are made using superelastic alloys (e.g., nickel titanium) and heat treated in specific ways.

The above and other needs are met by a method for modifying a physical characteristic of an endodontic instrument, the method comprising the steps of (a) placing at least one endodontic instrument made from at least about 50% by mass of a superelastic metal alloy into a salt bath oven containing a salt; (b) maintaining the temperature of the salt within the salt bath oven at a temperature ranging from about 475° C. to about 550° C. for a duration of from about four hours to about six hours; (c) maintaining the pH of the salt at a value ranging from about 6.9 to about 8.0; (d) allowing the salt bath to cool to a temperature below the melting point of the salt in the salt bath oven; and (e) removing the at least one endodontic instrument from the salt bath oven.

Preferably, the salt used in the salt bath consists essentially of a water soluble salt. Also, preferably, the at least one endodontic instrument consists essentially of a nickel titanium alloy. Additionally or alternatively, step (a) may further comprise the sub-step of placing the at least one endodontic instrument into the salt bath oven containing the salt, wherein the salt comprises a member selected from the group consisting of sodium nitrate, potassium nitrate, rubidium nitrate, magnesium nitrate, calcium nitrate, strontium nitrate, and barium nitrate. Additionally or alternatively, step (b) may further comprise the sub-step of maintaining the temperature of the salt within the salt bath oven at a temperature at about 500° C. of from about four and one-half hours to about five and one-half hours. Additionally or alternatively, step (b) may further comprise the sub-step of maintaining the temperature of the salt within the salt bath oven at a temperature ranging from about 500° C. to about 525° C. for a duration of from about four and one-half hours to about five and one-half hours.

In another aspect, the disclosure provides a method for modifying a physical characteristic of an endodontic instrument, the method comprising the steps of (a) placing at least one endodontic instrument made from at least about 50% by mass of a superelastic metal alloy into a salt bath oven containing a salt; (b) maintaining the temperature of the salt within the salt bath oven at a temperature ranging from about 475° C. to about 550° C. for a duration of at least about five hours; (c) maintaining the pH of the salt at a value ranging from about 6.5 to about 8.0 while the salt in the salt bath oven is molten; (d) allowing the salt bath to cool to a temperature below the melting point of the salt in the salt bath oven; and (e) removing the at least one endodontic instrument from the salt bath oven.

Step (a) may further comprise the sub-step of placing the at least one endodontic instrument into the salt bath oven containing the salt, wherein the salt comprises a member selected from the group consisting of sodium nitrate, potassium nitrate, rubidium nitrate, magnesium nitrate, calcium nitrate, strontium nitrate, and barium nitrate. Additionally or alternatively, step (c) may further comprise the sub-step of maintaining the pH of the salt at an average value ranging from about 6.9 to about 7.5 while the salt in the salt bath oven is molten wherein potassium dichromate is added to raise the pH as needed to maintain the pH in the claimed range

BRIEF DESCRIPTION OF THE DRAWINGS

Further features, aspects, and advantages of the present disclosure will become better understood by reference to the following detailed description, appended claims, and accompanying figures, wherein elements are not to scale so as to more clearly show the details, wherein like reference numbers indicate like elements throughout the several views, and wherein:

DETAILED DESCRIPTION

The terms "oven" and "furnace" are both broadly defined herein synonymously as an apparatus used to heat the contents therein to high temperatures (i.e., x>250° C.).

Figure 1:
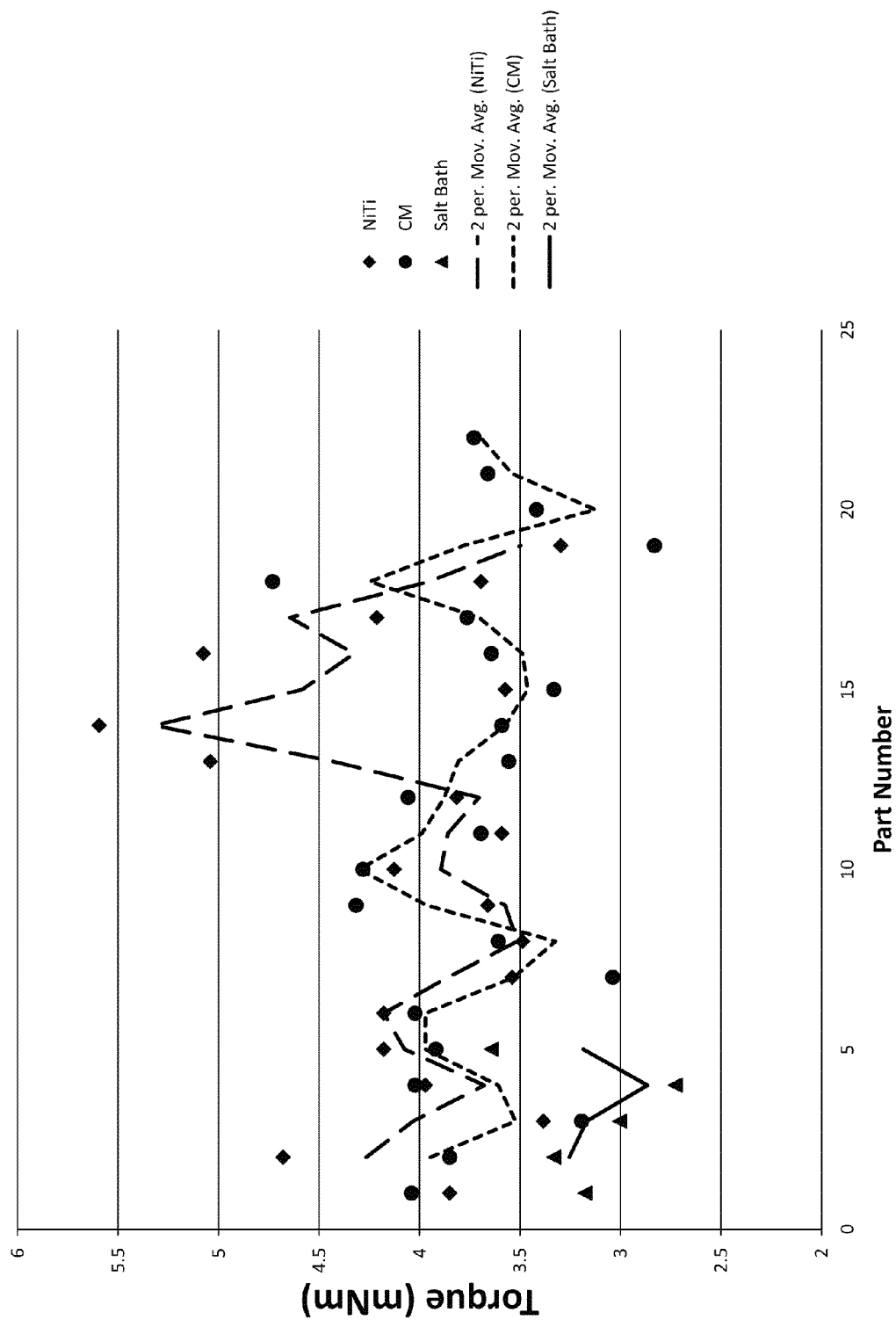
FIG. 1 shows a graph with plotted angular deflection data for NiTi instruments of three categories including untreated NiTi instruments, NiTi instruments heat treated in air under controlled conditions, and NiTi instruments treated in a salt bath under controlled conditions.
Figure 2:
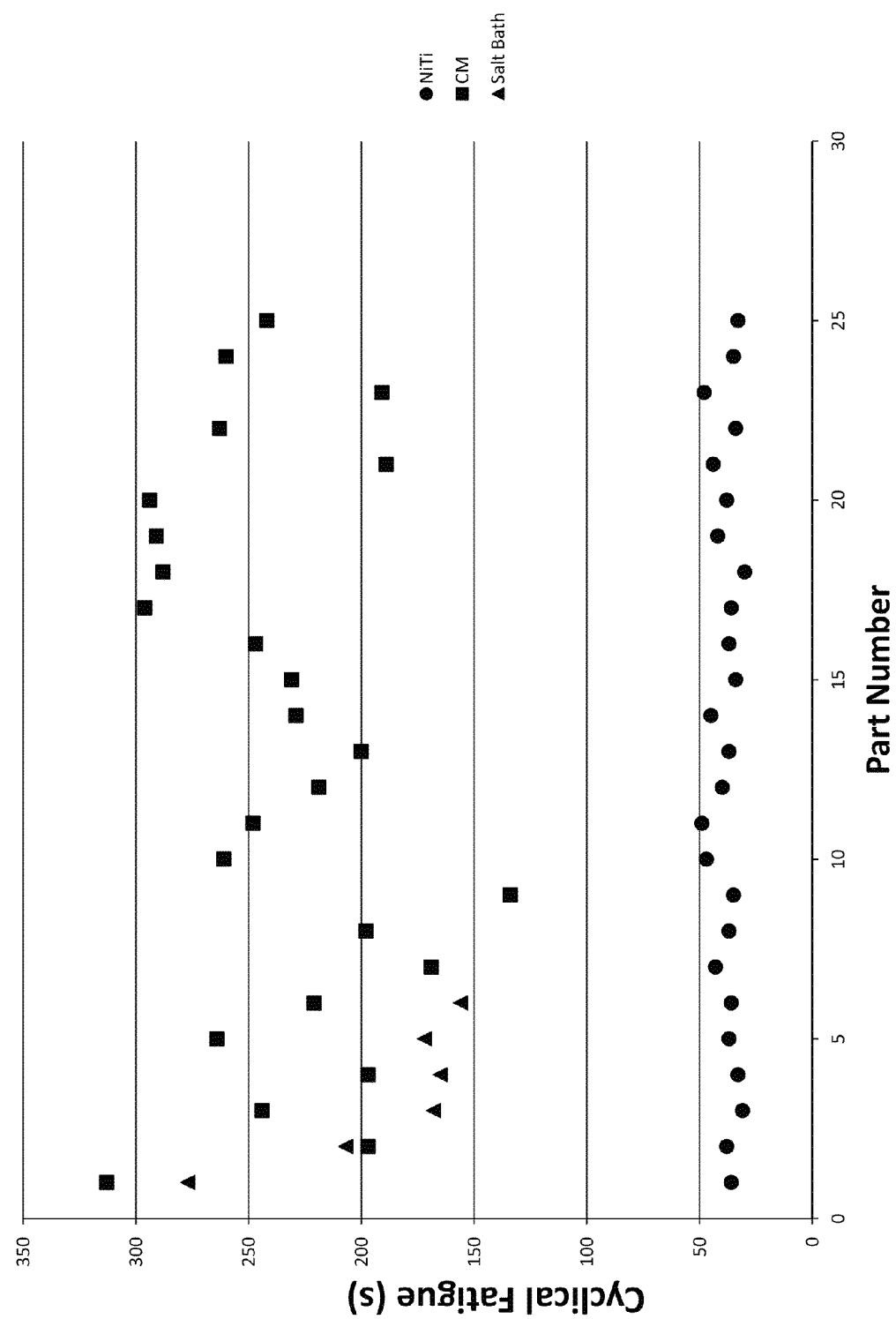
FIG. 2 shows a graph with plotted cyclical fatigue data for NiTi instruments of three categories including untreated NiTi instruments, NiTi instruments heat treated in air under controlled conditions, and NiTi instruments treated in a salt bath under controlled conditions.
Figure 3:
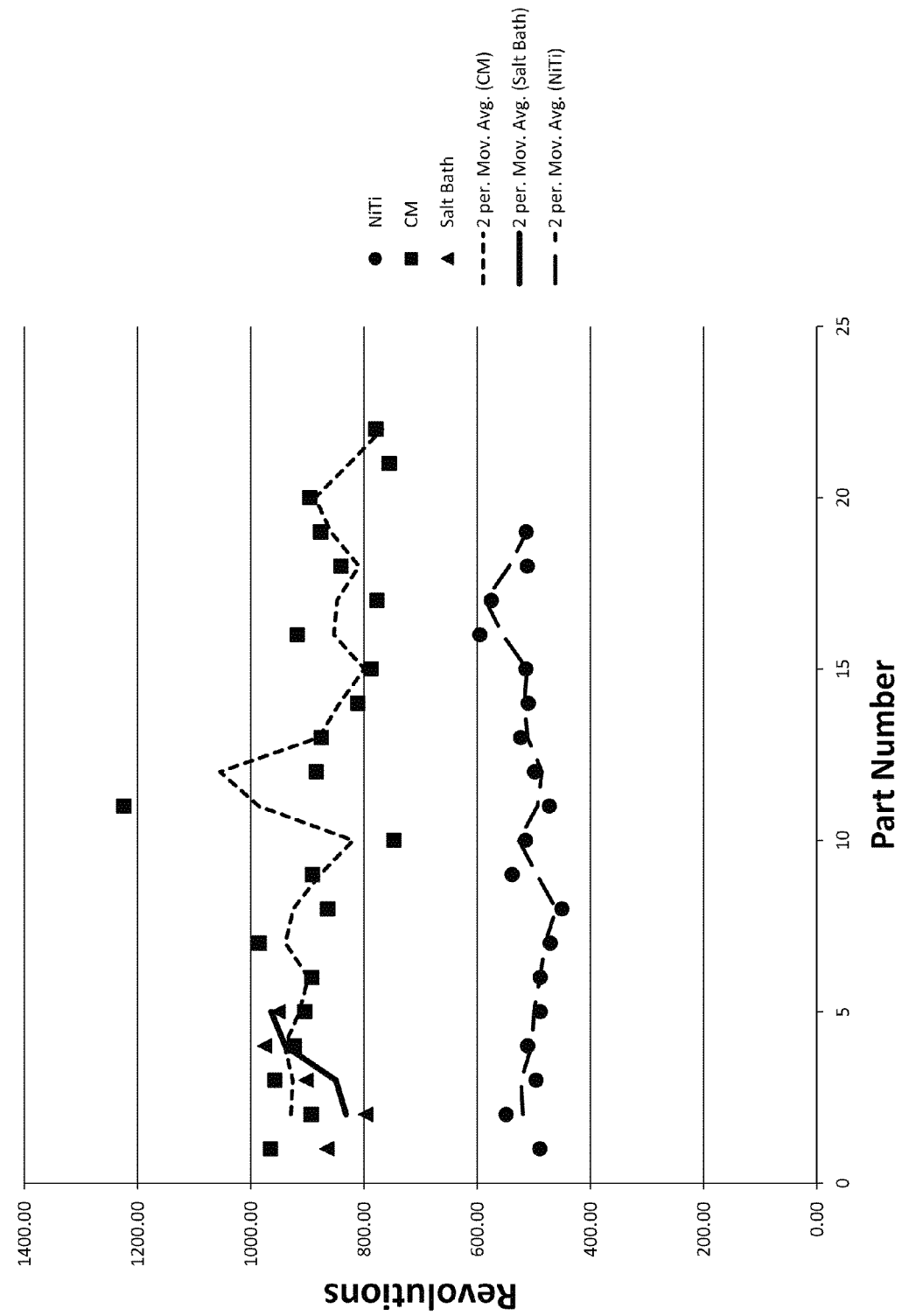
FIG. 3 shows a graph with plotted torque data for NiTi instruments of three categories including untreated NiTi instruments, NiTi instruments heat treated in air under controlled conditions, and NiTi instruments treated in a salt bath under controlled conditions.

FIGS. 1-3 show graphs with plotted data for nickel titanium ("NiTi") endodontic instruments of three categories including untreated NiTi instruments, NiTi instruments heat treated in air under controlled conditions, and NiTi instruments treated in a salt bath under controlled conditions. The Typhoon™ brand nickel titanium endodontic 25/04 instruments that were tested were all fluted and cut to final length. The data in FIG. 1 relate to angular deflection measurements, the data in FIG. 2 relate to cyclical fatigue measurements at 60° C., and the data in FIG. relate to torque measurements. The NiTi instruments treated in air were treated according to the methods described in U.S. Patent Application Publication Number 2011/0159458 entitled "Endodontic Instrument with Modified Memory and Flexibility Properties and Method" to Heath et al., the entirety of which is incorporated herein by reference. More specifically, the instruments heated in air were heated in a Thermolyne™ brand oven for approximately five hours and held at a temperature of a approximately 500° C.

Figure 4A:
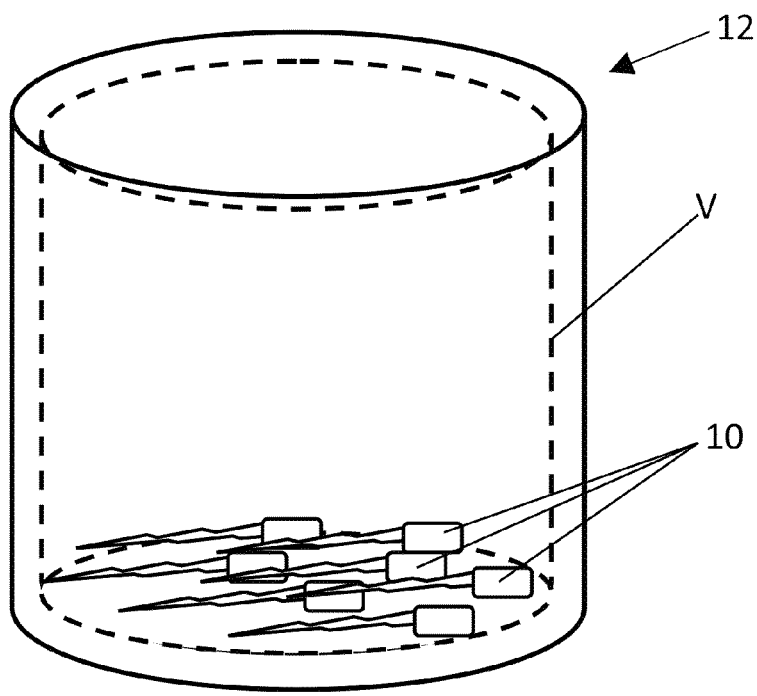
FIG. 4A shows an air heat treatment chamber of volume "V" with finished endodontic instruments positioned for heat treatment therein.
Figure 4B:
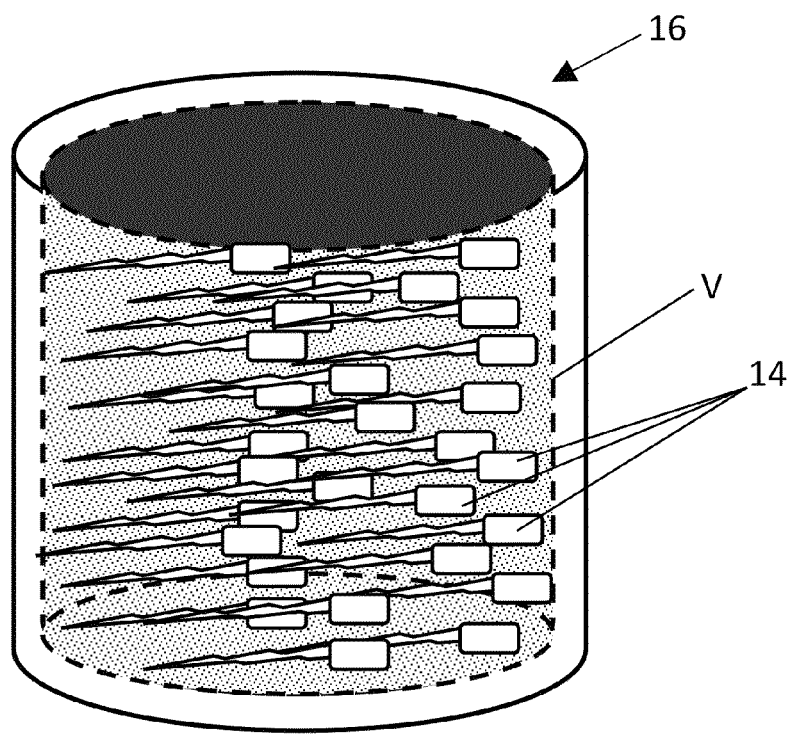
FIG. 4B shows a molten salt bath heat treatment chamber of volume "V" with finished endodontic instruments positioned for heat treatment therein.

Applicants hypothesized that using salt baths with minimal to no moisture content might provide a way to heat treat finished endodontic instruments to invoke controlled memory characteristics into such instruments and potentially minimize any oxidative effects from oxygen found, for example, in methods involving air heated instruments. Applicant's surprisingly found that, contrary to teachings in the prior art, endodontic instruments heat treated using the method described herein showed very limited signs of corrosion from exposure to salt in salt baths. Applicants also determined that the use of a salt bath as a heat treatment medium for endodontic instruments could also be a viable alternative to using heated air because a larger number of instruments per unit volume could be heat treated at one time using a salt bath as demonstrated, for comparative example, in FIGS. 4A and 4B. In FIG. 4A, a group of endodontic instruments 10 are shown schematically being treated in a first treatment chamber 12 including first volume "V" of heated air. Because of the low density of air (~0.54 grams/Liter at a temperature of 773.15 K), only a limited number of instruments can be included in the first treatment chamber 12. FIG. 4B shows a much larger number of endodontic instruments 14 being heat treated in a second treatment chamber 16 of a salt bath furnace, the second treatment chamber 16 holding molten salt which has been heated to approximately 500° C. in the same volume "V". As FIGS. 4A-4B show, the second treatment chamber 16 including molten salt can be used treat more instruments per volume than the treatment chamber 14 holding only hot air because the density of the molten salt is approximately five magnitudes greater than the density of air at about 500° C.

One example of a salt treatment that can be used is Quick Cure™ 420 available from Hubbard-Hall, Inc. of Waterbury, Conn. Quick Cure 420 is said to comprise a eutectic mixture of nitrate salts wherein a small amount of potassium dichromate may be added to raise the pH of the bath. Quick Cure 420 has an operating temperature range in molten form of from about 260° C. to about 600° C. Although a specific example is given herein, other salts that remain molten in a temperature range including about 500° C. are contemplated for use with the methods described herein. A salt mixture that is soluble in water is preferred for easy cleaning of a treatment chamber after a heat treatment.

One example of the methods described herein includes placing a plurality of endodontic instruments into a treatment chamber of, for example, a salt bath furnace wherein the temperature of the salt is maintained at a temperature ranging from about 475° C. to about 550° C., more preferably from about 500° C. to about 525° C., and most preferably about 500° C. The plurality of endodontic instruments are treated for a duration ranging from about four hours to about six hours, and more preferably from about four and one-half hours to about five and one-half hours. The salt bath is then allowed to cool to below its melting point and the endodontic instruments are removed. Preferably, water is used to remove any residual salt clinging to the instruments after they are removed. As such, water-soluble salts are preferred. In this preferred embodiment, the salt is reusable for future heat treatments.

A second example includes the steps of placing a plurality of endodontic instruments into a treatment chamber in a salt bath furnace containing an alkali nitrate salt wherein the temperature of the salt is maintained at a temperature ranging from about 475° C. to about 550° C., more preferably from about 500° C. to about 525° C., and most preferably about 500° C. The plurality of endodontic instruments is treated for a duration of at least about five hours. The average pH of the molten salt is preferably maintained at an average pH value ranging from about 6.9 to about 7.5. Potassium dichromate ($K_2Cr_2O_7$) or other suitable oxidizing agent can be added to the molten salt in small amounts to raise the pH of the molten salt as needed to keep the pH within the desired range. The salt bath is then allowed to cool to below its melting point and the endodontic instruments are removed. Preferably, water is used to remove any residual salt clinging to the instruments after they are removed.

The instruments that are most effectively modified when treated by the method described herein are made primarily of NiTi alloy wherein such alloy includes from about 53% (mass) to about 58% (mass) Nickel and from about 42% (mass) to about 47% (mass) Titanium. Preferably, such instruments are made of substantially 100% NiTi. Otherwise, such instruments should include at least about 50% (mass) NiTi.

The methods described herein are useful to modify the physical characteristics of the treated endodontic instruments and giving such instruments limited memory characteristics as described, for example, in U.S. Patent Application Publication Number 2011/0159458 to Heath et al. entitled "Endodontic Instrument with Modified Memory and Flexibility Properties and Method," cited above. However, the embodiments described herein minimize oxidative effects from treatment in air with direct exposure to oxygen. Prior attempts have been made to avoid such oxidative effects by limiting the treatment to a controlled atmosphere including non-reactive gases (e.g., nitrogen or noble gases such as, for example, argon) as described, for example, in U.S. Pat. No. 8,062,033 to Luebke entitled "Dental and Medical Instruments Comprising Titanium" and U.S. Pat. No. 8,083,873 to Luebke entitled "Dental and Medical Instruments Comprising Titanium." However, these prior techniques described in the Luebke references require the use of sealed environments of gases considered to be hazardous by OSHA as potentially causing rapid suffocation. As such, Applicants' embodiments described herein provide a way to heat multiple endodontic instruments in a limited volume with minimum exposure to oxygen and without the dangers associated with using unreactive gases in sealed environments as taught, for example, in the Luebke references. Moreover, unlike unreactive gases used in sealed chambers, when water soluble salt is used, the salt itself is recyclable and ready to use in subsequent heat treatments. Therefore, Applicant's surprisingly have found a way to use a molten salt bath—something that was previously thought to be undesirable for heat treating metal for medical instruments—in a way that improves on the safety and maintains or exceeds the efficacy of heat treatments of finished endodontic instruments to modify the physical characteristics of such instruments.

The foregoing description of preferred embodiments of the present disclosure has been presented for purposes of illustration and description. The described preferred embodiments are not intended to be exhaustive or to limit the scope of the disclosure to the precise form(s) disclosed. Obvious modifications or variations are possible in light of the above teachings. The embodiments are chosen and described in an effort to provide the best illustrations of the principles of the disclosure and its practical application, and to thereby enable one of ordinary skill in the art to utilize the concepts revealed in the disclosure in various embodiments and with various modifications as are suited to the particular use contemplated. All such modifications and variations are within the scope of the disclosure as determined by the appended claims when interpreted in accordance with the breadth to which they are fairly, legally, and equitably entitled.

What is claimed is:

1. A method for modifying a physical characteristic of an endodontic instrument, the method comprising the steps of:
   a. placing at least one endodontic instrument made from at least about 50% by mass of a superelastic metal alloy into a salt bath oven containing a salt;
   b. maintaining the temperature of the salt within the salt bath oven at a temperature ranging from about 475° C. to about 550° C. for a duration of from about four hours to about six hours;
   c. maintaining the pH of the salt at a value ranging from about 6.9 to about 8.0;
   d. allowing the salt bath to cool to a temperature below the melting point of the salt in the salt bath oven; and
   e. removing the at least one endodontic instrument from the salt bath oven.

2. The method of claim 1 wherein the at least one endodontic instrument consists essentially of a nickel titanium alloy.

3. The method of claim 1 wherein the salt used in the salt bath consists essentially of a water soluble salt.

4. The method of claim 1 wherein step (b) further comprises maintaining the temperature of the salt within the salt bath oven at a temperature ranging from about 500° C. to about 525° C. for a duration of from about four and one-half hours to about five and one-half hours.

5. The method of claim 1 wherein step (b) further comprises maintaining the temperature of the salt within the salt bath oven at a temperature of about 500° C. for from about four and one-half hours to about five and one-half hours.

6. The method of claim 1 wherein step (a) further comprises placing the at least one endodontic instrument into the salt bath oven containing the salt, wherein the salt comprises a member selected from the group consisting of sodium nitrate, potassium nitrate, rubidium nitrate, magnesium nitrate, calcium nitrate, strontium nitrate, and barium nitrate.

7. A method for modifying a physical characteristic of an endodontic instrument, the method comprising the steps of:
   a. placing at least one endodontic instrument made from at least about 50% by mass of a superelastic metal alloy into a salt bath oven containing a salt;
   b. maintaining the temperature of the salt within the salt bath oven at a temperature ranging from about 475° C. to about 550° C. for a duration of at least about five hours;
   c. maintaining the pH of the salt at a value ranging from about 6.5 to about 8.0 while the salt in the salt bath oven is molten;
   d. allowing the salt bath to cool to a temperature below the melting point of the salt in the salt bath oven; and
   e. removing the at least one endodontic instrument from the salt bath oven.

8. The method of claim 7 wherein step (a) further comprises placing the at least one endodontic instrument into the salt bath oven containing the salt, wherein the salt comprises a member selected from the group consisting of sodium nitrate, potassium nitrate, rubidium nitrate, magnesium nitrate, calcium nitrate, strontium nitrate, and barium nitrate.

9. The method of claim 8 wherein step (c) further comprises maintaining the pH of the salt at an average value ranging from about 6.9 to about 7.5 while the salt in the salt bath oven is molten wherein potassium dichromate is added to raise the pH as needed to maintain the pH in said range.

* * * * *

UNITED STATES PATENT AND TRADEMARK OFFICE
CERTIFICATE OF CORRECTION

PATENT NO.        : 9,005,377 B2
APPLICATION NO.   : 13/917038
DATED             : April 14, 2015
INVENTOR(S)       : Derek E. Heath et al.

It is certified that error appears in the above-identified patent and that said Letters Patent is hereby corrected as shown below:

ON THE TITLE PAGE

Page 1, Item (60), first line - "61/658,959" should read "61/658,969"

IN THE SPECIFICATION

Column 1, line 9 - "61/658,959" should read "61/658,969"

Signed and Sealed this
Fifteenth Day of March, 2016

Michelle K. Lee
*Director of the United States Patent and Trademark Office*